United States Patent [19]

Moser et al.

[11] 4,103,016
[45] Jul. 25, 1978

[54] ANTIINFLAMMATORY IMIDAZOTHIAZOLES AND THIAZOLOPYRIMIDINES

[75] Inventors: Robert E. Moser, Mentor; Larry J. Powers, Madison; Zaven S. Ariyan, Mentor, all of Ohio

[73] Assignee: Diamond Shamrock Corporation, Cleveland, Ohio

[21] Appl. No.: 753,350

[22] Filed: Dec. 22, 1976

Related U.S. Application Data

[63] Continuation-in-part of Ser. No. 650,318, Jan. 19, 1976, Pat. No. 4,041,167.

[51] Int. Cl.$^2$ .................. A61K 31/425; C07D 277/00
[52] U.S. Cl. ............................ 424/270; 260/306.7 T
[58] Field of Search .................. 424/270; 260/306.7 T

[56] References Cited

U.S. PATENT DOCUMENTS

| 4,008,245 | 2/1977 | Acheson et al. ............. 260/306.7 T |
| 4,042,583 | 8/1977 | Acheson et al. ............. 260/306.7 T |

*Primary Examiner*—Stanley J. Friedman
*Attorney, Agent, or Firm*—Stuart L. Melton

[57] ABSTRACT

Certain imidazothiazoles and thiazolopyrimidines have been found to prevent and inhibit the formation of granuloma tissue in animals. This result is accomplished by administering to the animal subject a therapeutically effective amount of a compound having the formula:

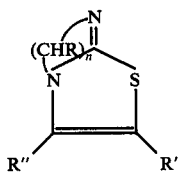

wherein R is hydrogen or methyl, R' is hydrogen, lower alkyl or thioalkyl, carboxy methyl, or phenyl; R'' is lower alkyl, 2-benzofuranyl, naphthyl, phenyl, or mono- or disubstituted phenyl. The hydrated precursors of certain of these compounds as well as the acid addition and quaternary salts of both the compounds and their hydrated precursors may be employed.

10 Claims, No Drawings

ANTIINFLAMMATORY IMIDAZOTHIAZOLES AND THIAZOLOPYRIMIDINES

CROSS REFERENCE TO RELATED APPLICATIONS

This application is a continuation-in-part of copending application Ser. No. 650,318, filed Jan. 19, 1976, now U.S. Pat. No. 4,041,167.

BACKGROUND OF THE INVENTION

Many compounds are known which exhibit some degree of antiinflammatory activity.

For example, British Pat. No. 1,099,389 discloses certain 2,4-disubstituted thiazoles which are known to be antiinflammatory. However, these compounds suffer from certain inherent deficiencies which limit their utility as antiinflammatory drugs. Also, in U.S. Pat. No. 3,796,800 is disclosed another group of thiazoles which exhibit antiinflammatory properties. These compounds are generally identified by the formula:

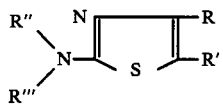

wherein R is lower alkyl (e.g., —CH$_3$), or N-aminocarbamoyl; R" and R"' are independently selected from the group consisting of hydrogen, lower alkyl (e.g., —C$_2$H$_5$) and lower acyl (e.g., —COCH$_3$); and R' is hydrogen, CONHR$_1$ or CONR$_2$R$_3$, wherein R$_1$ is phenyl, mono-, di- or tri-(lower) alkylphenyl, cyclohexyl, or amino; R$_2$ is lower alkyl (C$_1$-C$_3$); R$_3$ is lower alkyl (C$_2$-C$_3$) or phenyl; or R$_2$ and R$_3$ together with the nitrogen atom form a morpholino ring, and pharmaceutically acceptable acid addition salts thereof, such as the hydrochloride.

While the above compounds evidence antiinflammatory properties, they also exhibit certain other properties which limit their utility as such drugs.

From the Canadian Journal of Chemistry (Vol. 42, pg. 2847, 1969) certain [2,1-b] thiazoles and thiazolo [3,2-a] pyrimidines are known as anthelmintics. 3-(Hydroxy- or methoxy)-phenyl-5,6-dihydroimidazo-[2,1-b] thiazoles are known from U.S. Pat. No. 2,969,369 to have a variety of pharmaceutical activities, including an antiinflammatory effect. Further, U.S. Pat. No. 3,860,718 describes the use of quaternary 7-substituted imidazo [2,1-b] thiazolium compounds as hypoglycemic agents (blood-sugar lowering agents), but no disclosure can be found therein which would indicate that such compounds have antiinflammatory properties.

STATEMENT OF THE INVENTION

Therefore, it is an object of the present invention to provide effective antiinflammatory compositions containing as the active ingredients thereof certain imidazothiazoles and thiazolopyrimidines.

It is a further object of the present invention to provide a method for preventing and inhibiting the formation of granuloma tissue in animals employing certain imidazothiazoles and thiazolopyrimidines.

It is a still further object of the present invention to provide an imidazothiazole and certain hydrated precursors of imidazothiazoles and thiazolopyrimidines which have pharmaceutical activity.

These and further objects of the present invention will become apparent to those skilled in the art from the specification and claims which follow.

There has now been found a pharmaceutical preparation in dosage unit form, the active ingredient of which consists of a nontoxic antiinflammatory amount of at least one compound of the formula:

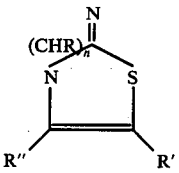

wherein $n$ is 2 or 3; R is hydrogen or methyl; R' is hydrogen, C$_1$-C$_3$ alkyl or thioalkyl, phenyl, or carboxy methyl; and R" is C$_1$-C$_4$ alkyl, 2-benzofuranyl, naphthyl, phenyl, or mono- or disubstituted phenyl, and acid addition and quaternary salts thereof.

Further in accordance with the objects and practices of the present invention, there have been found active antiinflammatory compounds and mixtures thereof and pharmaceutical preparations in nontoxic dosage unit form adapted for oral or parenteral administration comprised of compounds of the formula:

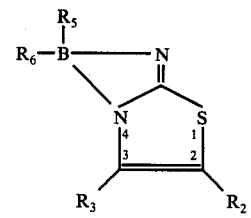

wherein B is ethylene, vinylene (—CH=CH—) or 1',2'-cyclohexylene and
when
B is ethylene
R$_2$ is C$_1$-C$_3$ alkylsulfonyl or a group of the formula

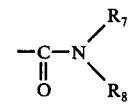

where R$_7$ and R$_8$ are independently selected from hydrogen, monofluorophenyl, trifluoromethylphenyl, or trimethylphenyl with the proviso that R$_7$ and R$_8$ can not simultaneously be hydrogen, or R$_7$ and R$_8$ when taken together with the nitrogen atom to which they are attached form cis-dimethylpyrrolidine; R$_3$ is C$_1$-C$_4$ alkyl (preferably methyl) or phenyl; R$_5$ and R$_6$ are each independently selected from hydrogen or C$_1$-C$_4$ alkyl (preferably methyl); and
when
B is vinylene
R$_2$ is hydrogen; R$_3$ is hydrogen or C$_1$-C$_4$ alkyl; R$_5$ and R$_6$ are independently selected from hydrogen, phenyl, bromo- or nitrophenyl (preferably para substituted) with the proviso that R$_5$ and R$_6$ can not simultaneously be hydrogen; and
when
B is 1',2'-cyclohexylene $R_2$ is hydrogen and $R_3$ is $C_1$-$C_4$ alkyl (preferably methyl) or phenyl and $R_5$ and $R_6$ are each hydrogen with the proviso that when $R_3$ is methyl the bond at the 2,3-position of the thiazole ring may be saturated and the C-3 carbon atom thereof optionally substituted by a hydroxyl group;

and the pharmaceutically acceptable inorganic or organic acid addition and quaternary salts thereof.

A method of preventing and inhibiting the formation of granuloma tissue in an animal subject has further been found, which method comprises administering to said animal a nontoxic antiinflammatory amount of at least one such compound or pharmaceutical preparation thereof.

There have further been found 3-(2-benzofuranyl)-5,6-dihydro-4H-imidazo-[2,1-b] thiazole and certain hydrated precursors of imidazothiazoles and thiazolopyrimidines having the formula:

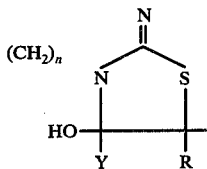

wherein $n$ is 2 or 3; R is H or $CH_3$; and Y is phenyl or p-chloro- or p-methoxyphenyl. These compounds also have antiinflammatory effect and may be employed in the acid addition or quaternary salt form.

DESCRIPTION OF THE PREFERRED EMBODIMENTS

Compounds which are the active ingredients of the present invention fit the general formula:

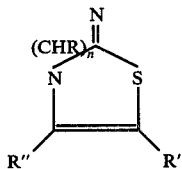

In this formula, when $n$ is 2, the compounds are designated generally as substituted 5,6-dihydro-4H-imidazo-[2,1-b] thiazoles. When $n$ is 3, the compounds are designated as substituted tetrahydrothiazolo-[3,2-a] pyrimidines. The substituent R, of which 1 may be present on each methylene group, represents either hydrogen or methyl. The groups represented by R' include hydrogen, $C_1$-$C_3$ alkyl (especially methyl and ethyl) and thioalkyl (especially thiomethyl), carboxy methyl; and phenyl. The members fitting the definition of R" include $C_1$-$C_4$ alkyl (especially methyl and tertiarybutyl), 2-benzofuranyl, naphthyl, phenyl, and mono- or disubstituted phenyl (especially wherein the substituents are electronegative and in the "para" position, such as Cl, Br, $NO_2$, $OCH_3$, and 3,4-dichloro- or dimethyl). A preferred and novel compound at this time is 3-(2-benzofuranyl)-5,6-dihydro-4H-imidazo [2,1-b] thiazole (including salts thereof). Preferred and novel hydrated precursors of the above formula are those corresponding to the formula:

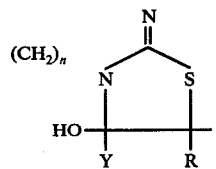

wherein $n$ is 2 or 3; R is H or methyl; and Y is phenyl or p-chloro- or p-methoxyphenyl.

As exemplary specifically preferred compounds of the formula

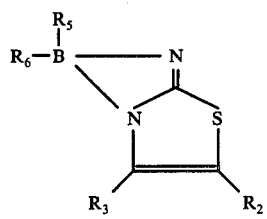

and salts thereof referred to above, there may be mentioned 2',4',6'-trimethyl-3-methyl-5,6-dihydro-4H-imidazo-[2,1-b] thiazole-2-carboxanilide, 2'-fluoro-3-methyl-5,6-dihydro-4H-imidazo-[2,1-b] thiazole-2-carboxanilide, 3'-trifluoromethyl-3-methyl-5,6-dihydro-4H-imidazo-[2,1-b] thiazole-2-carboxanilide, 2',4',6'-trimethyl-3,4 (or 3,5)-dimethyl-5,6-dihydro-4H-imidazo-[2,1-b] thiazole-2-carboxanilide, 2',4',6'-trimethyl-3-phenyl-5,6-dihydro-4H-imidazo-[2,1-b] thiazole-2-carboxanilide, cis-2',5'-dimethyl-3-methyl-5,6-dihydro-4H-imidazo-[2,1-b] thiazole-2-pyrrolidamide, 6-phenyl (or 6-phenyl-3-methyl)-4H-imidazo-[2,1-b] thiazole and the corresponding 7-(4"-chlorobenzyl) thiazolonium chlorides, 6-(4'-nitrophenyl)-4H-imidazo-[2,1-b] thiazole, 6-(4'-bromophenyl)-4H-imidazo-[2,1-b] thiazole and the corresponding 7-(2",4"-dichlorobenzyl), (2"-chlorobenzyl) or (3"-propargyl) thiazolonium chlorides, cis-3-methyl-4,5,6,7,8,9,-hexahydrobenzimidazole thiazole, trans-3-methyl-4,5,6,7,8,9-hexahydrobenzimidazole thiazole, trans-3-methyl-3-hydroxy-2,3,4,5,6,7,8,9-octahydrobenzimidazole thiazole corresponding, respectively, to the structural formulas

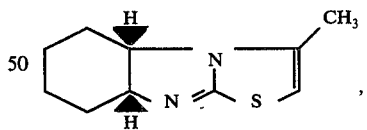

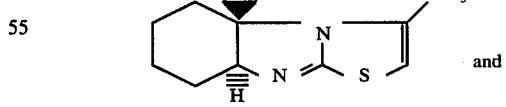

and

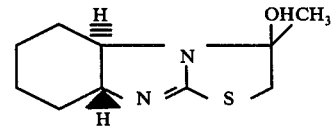

as well as the stereoisomeric random mixtures thereof and the pharmaceutically acceptable inorganic and organic acid addition salts and quaternary salts of the foregoing such as, for instance, the hydrochloride, hydrobromide, tartrate, phosphate or alkyl or aralkyl halides, i.e., propargyl bromide, mono- or dihalobenzyl chloride, and the like.

While the compounds themselves exhibit excellent antiinflammatory activity, they may be and often are employed in the form of pharmacologically acceptable acid addition or quaternary salts thereof. For example, one may employ acid halides, such as HBr or HCl, or tartaric acid, to form the addition salts or alkyl halides and the like, such as propargyl bromide, for quaternization. The criteria for choosing and methods for preparing salts suitable for administration are well known to those skilled in the art.

In preparing the pharmaceutical compositions of the present invention in unit dosage form, a nontoxic, antiinflammatory amount of one or more of the compounds of the present invention is incorporated with the appropriate carriers and/or diluents. Generally, the amount for administration will be from about 10 to 500 milligrams/kilogram/day of body weight, preferably from about 50 to 300 mg/kg/day.

For example, in the case of a tablet, the composition will comprise, in addition to the active ingredient, fillers, binders, and diluents such as lactose, methylcellulose, talc, gum tragacanth, gum acacia, agar, polyvinylpyrrolidone, stearic acid, and/or corn starch, etc. In the case of a liquid suspension for oral administration, the composition will comprise, in addition to the active ingredients, a filler such as sodium carboxymethylcellulose and/or syrup, e.g., a glycerine based syrup. In the case of a parenteral solution or suspension, the composition will comprise, in addition to the active ingredient, a suitable solvent or other liquid such as a saline solution. In the case of a topical ointment, a vehicle such as petroleum jelly or hydrophillic petroleum is suitable.

The compounds employed in the instant invention may be prepared by the condensation of an α-haloketone with (1) 2-mercaptoimidazoline or a substituted derivative to yield the desired (substituted) 5,6-dihydro-4H-imidazo-[2,1-b] thiazole or (2) with 1,2,3,4-tetrahydro-2-pyrimidinethiol or a substituted derivative to yield the desired (substituted) tetrahydrothiazolo-[3,2-a] pyrimidine. Reference to such standard preparations is set forth in the Canadian Journal of Chemistry, Vol. 47 (1969) at page 2843.

The 2-carboxanilide derivatives of the invention may be synthesized by allowing the appropriate 2-mercaptoimidazole to react with a 2-chloro-acetoacetanilide in refluxing alcohol. The 2-chloro-acetoacetanilides can be conventionally prepared by chlorination of the corresponding acetoacetanilide with sulfuryl chloride in benzene. The acetoacetanilide starting materials can be obtained by heating ethyl acetoacetate with a substituted aniline.

Generally, the cis and trans isomers of 3-methyl-4,5,6,7,8,9-hexahydrobenzimidazole thiazole can be obtained by the following stereospecific synthesis method. Commercially available diaminocyclohexane (cis-trans mixture) is separated into the respective stereoisomers according to the procedure of R. Saito and Y. Kidani, *Chemistry Letters*, 123–126 (1976). The pure stereoisomers (cis or trans) are then allowed to react with carbon disulfide in ethanol-water. After treatment with concentrated HCl, 2-mercapto-4,5,6,7,8,9-hexahydrobenzimidazole is obtained. If the 2-mercaptobenzimidazole is allowed to react with chloroacetone at 25° C, 3-methyl-3-hydroxy-octahydrobenzimidazo thiazoles are obtained. However, if the 2-mercaptoimidazole is allowed to react with chloroacetone in refluxing ethanol, 3-methyl hexahydrobenzimidazo thiazoles are obtained. Examples of the preparation of certain compounds of the instant invention follow.

EXAMPLE 1

To a refluxing solution of 3-benzoyl propionic acid (18g) in CHCl$_3$ (100 ml) was added bromine (16.2 g) in CHCl$_3$ (100 ml). After 10 minutes of refluxing, the reaction mixture was cooled and the CHCl$_3$ removed in vacuo. 2-Mercapto-imidazolidine (10.2 g) in absolute ethanol was added and the reaction mixture heated to reflux for 1 hour. The reaction mixture was cooled and the precipitate separated by filtration. The product was recrystallized from 95% ethanol. The isolated product (5.5 g) has a melting point of 258°–263° C and was found to be 3-phenyl-5,6-dihydro-4H-imidazo-[2,1-b] thiazo-2-yl-acetic acid hydrobromide.

EXAMPLE 2

Similarly, for the preparation of 2-methylthio-3-t-butyl-5,6-dihydro-4H-imidazo-[2,1-b] thiazole hydrobromide, the procedure of Example 1 was followed except 1-methylthiopinacolone (10.7 g) was brominated (11.4 g) for the desired intermediate.

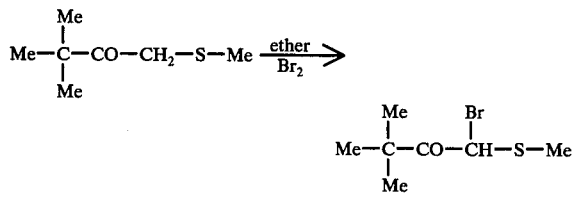

EXAMPLE 3

A solution of 7.41 g (0.05 mole) of N-butyrophenone and a trace of AlCl$_3$ in 15 ml anhydrous ethyl ether was brominated using 8.0 g (2.65 ml; 0.05 mole) of bromine. The ether and the bromine were removed in vacuo. The resulting oil was diluted to 100 ml with absolute ethanol and mixed with 5.809 g (0.05 mole) of 3,4,5,6-tetrahydro-2-pyrimidine thiol. This material was refluxed for 18 hours. The crude product which was obtained on cooling the reaction mixture was recrystallized from 95% ethanol. Recovery was 8.09 g (49.74%) of a white solid which was analyzed and found to be 2-ethyl-3-phenyl-4,5,6,7-tetrahydrothiazole[3,2-a] pyrimidine hydrobromide.

It should be noted that the intermediates, e.g., hydrated compounds, may be produced by well known variations of the foregoing general techniques. For example, they can be obtained by not refluxing but simply heating to a temperature of about 25° C.

EXAMPLE 4 m-Trifluoromethyl aniline (32.22 g) in benzene was dissolved in benzene and diketene added slowly with mixing. The reaction mixture was allowed to stand at 25° C. The resulting solid product was recrystallized from ethanol to yield 3'-trifluoromethyl acetoacetanilide.

EXAMPLE 5

3'-Trifluoromethyl acetoacetanilide (28.45 g) obtained in Example 4 was dissolved in warm benzene. Sulfuryl chloride (9.4 ml, 0.116 m) was added slowly and the reaction allowed to stand at 25° C for about 2 hours. The solvent was removed and the residual oil was dissolved in ethanol (absolute-100 ml) and ethylene thiourea (11.8 g-.116 m) added. The mixture was then refluxed for 2 hours and the solid which separated on cooling was filtered, dried and recrystallized from absolute ethanol to yield 36.2 g of 3-methyl-3'-trifluoromethyl-5,6-dihydro-4H-imidazo-[2,1-b] thiazole-2-carboxanilide hydrochloride (m.p. 271°-275° C).

EXAMPLE 6

2',4',6'-Trimethylbenzoylacetanilide (17.5 g-.062 m) was slurried in 250 ml hot benzene and 8.4 g of sulfuryl chloride slowly added to the solution. Upon standing for approximately 2 hours, the reaction mixture yielded a heavy white precipitate which was removed by filtration and dried. 17 g (.053 m) of the precipitate was then reacted with ethylene thiourea (5.4 g) in 350 ml absolute ethanol and allowed to reflux for about 25 hours. The solvent was stripped, yielding a yellow white solid which was recrystallized from ethyl acetate/methanol to give 9.9 g of the product 3-phenyl-2',4',6'-trimethyl-5,6-dihydro-4H-imidazo-[2,1-b] thiazole 2-carboxanilide hydrochloride (m.p. 270°-271° C).

EXAMPLE 7

Trans-diaminocyclohexane (20 g) in ethanol-water (50 ml; 50%) was heated to 60° C. Carbon disulfide (16 ml) was then added dropwise over a 1 hour period. After refluxing for 1 hour, concentrated HCl (1.5 ml) was added and the mixture refluxed for 18 hours. The hot reaction mixture was poured into an Erlenmeyer flask and cooled to 5° C for 2 hours. The resulting precipate was separated by filtration and washed with 50% ethanol-water. The residue was dried to yield 16.74 g, m.p. 196°-197° C. The mother liquor was concentrated to yield another crop of crystals (m.p. 190°-5° C, 1.9 g) identified as trans-2-mercapto-4,5,6,7,8,9-hexahydrobenzimidazole.

EXAMPLE 8

Trans-2-mercapto-4,5,6,7,8,9-hexahydrobenzimidazole (2.0 g) obtained in Example 7 and chloroacetone (1.05 ml) were slurried in ethanol and the mixture heated to reflux for 18 hours. The reaction mixture was cooled and concentrated to about 20 ml. Diethylether (60 ml) was added to give a white precipitate. This was separated, washed with diethylether and dried to yield 2.31 g (78%), m.p. 212°-14° C, of trans-3-methyl-4,5,6,7,8,9-hexahydrobenzimidazole thiazole hydrochloride.

EXAMPLE 9

Trans-2-mercapto-4,5,6,7,8,9-hexahydrobenzimidazole (2.0 g) and chloroacetone was stirred in ethanol (40 ml) at 25° C for 18 hours. Diethylether (60 ml) was added to the reaction mixture and the resulting suspension cooled to 5° C. The solid was separated, dried and washed with diethylether to yield 2.54 g (80%) of trans-3-methyl-3-hydroxy-2,3,4,5,6,7,8,9-octahydrobenzimidazole thiazole.

EXAMPLE 10

The compounds of the present invention have pharmaceutical activity as antiinflammatory agents, effective in the prevention and inhibition of granuloma tissue formation. The activity is demonstrated by a test which involves the diminution of experimental edema induced in the hind paw of a rat by the injection of carrageenin.

The procedure used for measuring the inhibition of carrageenin-induced edema is a slight modification of the method of Winter et al., Proc. Soc. Exptl. Biol. Med. 111:544 (1962). The device used for measurement of the paw volume is an adaptation of the water displacement procedure described by Adamkiewicz et al., Can. J. Biochem. Physiol. 33:332 (1955). The above compounds were studied for their effectiveness in preventing the edema caused by the intraplantar injection of 0.05 ml of a sterile 1.0% solution of carrageenin. Compounds were administered orally, except when indicated as intraperitoneally (i.p.), one hour prior to the injection of the carrageenin into the left hind paw of rats. At peak swelling time (3 hours) the volume of edema was calculated by differential paw volumes.

Table I (in which Ph = phenyl) sets forth results obtained at the indicated dosages with compounds (or their salts) of the formula:

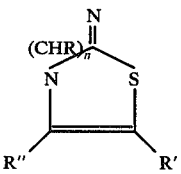

TABLE I

| Compound | n= | R= | R'= | R"= | Salt | Dose (mg/kg) | Reduction % |
|---|---|---|---|---|---|---|---|
| 1 | 2 | H,H | H | Ph | HBr | 50 | 47 |
| 2 | " | " | H | 3,4-diCH$_3$Ph | " | " | 27 |
| 3 | " | " | SCH$_3$ | C(CH$_3$)$_3$ | " | " | 26 |
| 4 | " | " | C$_2$H$_5$ | Ph | " | 25 | 41 |
| 5 | " | " | C$_2$H$_5$ | P-ClPh | " | " | 33 |
| 6 | " | " | CH$_3$ | " | " | " | 45 |
| 7 | " | " | H | p-BrPh | " | 50 | 70 |
| 8 | " | " | H | C(CH$_3$)$_3$ | H tartrate | " | 56 |
| 9 | " | " | H | CH$_3$ | HCl | " | 46 |
| 10 | " | " | H | α-naphthyl | HI | " | 58 |
| 11 | " | " | H | C(CH$_3$)$_3$ | none | " | 48 |
| 12 | " | CH$_3$,H | H | C(CH$_3$)$_3$ | HBr | " | 54 |
| 13 | " | CH$_3$,H | H | CH$_3$ | HCl | " | 24 |
| 14 | " | H,H | CH$_3$ | Ph | HBr | " | 49 |
| 15 | " | H,H | Ph | CH$_3$ | HBr | " | 53 |
| 16 | " | CH$_3$,H | H | p-ClPh | HBr | " | 58 |
| 17 | " | CH$_3$,H | H | p-NO$_2$Ph | HBr | " | 48 |
| 18 | " | CH$_3$,H | H | 3,4-diClPh | HBr | " | 42 |
| 19 | 2 | H,H | CH$_2$COOH | Ph | HBr | 100ip | 24 |
| 20 | " | " | H | Ph | 3,4-diCl-benzyl Cl | 20 | 36 |
| 21 | " | " | H | p-BrPh | none | 40 | 49 |
| 22 | " | " | H | " | propargyl Br | 100 | 36 |

TABLE I-continued

| Compound | n= | R= | R'= | R''= | Salt | Dose (mg/kg) | Reduction % |
|---|---|---|---|---|---|---|---|
| 23 | " | " | H | " | α-methyl propargyl Cl | 40 | 27 |
| 24 | " | " | H | " | 4-chloro-2-buteneyl Cl | 60 | 20 |
| 25 | " | " | H | $CH_3$ | none | 150 | 44 |
| 26 | " | " | H | $CH_3$ | propargyl Br | 40 | 31 |
| 27 | " | " | H | 2-benzofuranyl | HBr | 40 | 40 |
| 28 | 3 | 3H | H | p-ClPh | " | 25 | 29 |
| 29 | " | " | $C_2H_5$ | Ph | " | 50 | 76 |
| 30 | " | " | H | Ph | " | 40 | 25 |
| 31 | " | " | $CH_3$ | Ph | " | 40 | 48 |
| 32 | " | " | H | p-$NO_2$Ph | " | 25 | 20 |
| 33 | " | " | $CH_3$ | p-ClPh | " | 10 | 22 |

All compounds show a positive effect, which may be increased by the use of larger dosages.

EXAMPLE 11

Following the procedure set forth in Example 10, hydrated compounds according to the following formula were evaluated for antiinflammatory effect with the results shown in Table II:

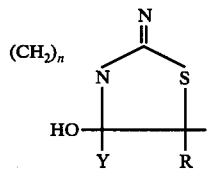

TABLE II

| Compound | n= | Y= | R= | Salt | Dose (mg/kg) | Reduction (%) |
|---|---|---|---|---|---|---|
| 34 | 2 | Ph | H | HBr | 100 | 70 |
| 35 | 2 | Ph | $CH_3$ | " | 150 | 68 |
| 36 | 2 | p-ClPh | H | " | 25 | 57 |
| 37 | 3 | Ph | H | " | 50 | 52 |
| 38 | 3 | p-ClPh | H | " | 100 | 76 |
| 39 | 3 | p-$CH_3$OPh | H | " | 40 | 27 |

EXAMPLE 12

Following the procedure set forth in Example 10, compounds according to the following formula were evaluated for antiinflammatory effect with the results shown in Table II-A:

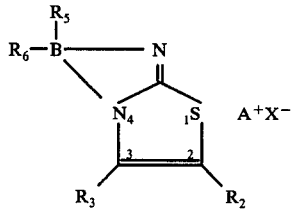

TABLE II-A

| B | $R_2$ | $R_3$ | $R_5$ | $R_6$ | A | X | Dose (mg/kg) | Reduction (%) |
|---|---|---|---|---|---|---|---|---|
| Ethylene | Me, -C(=O)-NH-(2,4,6-Me,Me substituted phenyl)-Me | $CH_3$ | H | H | H | Cl | 200 | 11 |
| " | -C(=O)-NH-(2-F phenyl) | $CH_3$ | H | H | H | Cl | 200 | 15 |
| " | -C(=O)-NH-(3-$CF_3$ phenyl) | $CH_3$ | H | H | H | Cl | 200 | 66 |
| " | $CH_3$, -C(=O)-NH-(2,4,6-tri$CH_3$ phenyl) | $CH_3$ | $CH_3$ | H | — | — | 200 | 24 |

TABLE II-A-continued

| B | R₂ | R₃ | R₅ | R₆ | A | X | Dose (mg/kg) | Reduction (%) |
|---|---|---|---|---|---|---|---|---|
| " | -C(=O)-N(pyrrolidinyl with 2,5-diCH₃) | C₆H₅ | H | H | H | | Cl | 50 | 23 |
| " | CH₃ | CH₃ | H | H | H | | Cl | 200 | 20 |
| " | -C(=O)-N(H)-(2,4,6-triCH₃-C₆H₂) | CH₃ | CH₃ | CH₃ | H | | Cl | 40 | 3 |
| " | SO₂CH₃ | C₆H₅ | H | H | — | | — | 200 | 43 |
| Vinylene | " | H | Ph | " | " | | " | 100 | 69 |
| " | " | " | " | " | p-ClC₆H₄CH₂— | | Cl⁻ | 40 | 22 |
| " | " | " | p-NO₂Ph | " | H | | Br⁻ | 200 | 28 |
| " | " | " | p-BrPh | " | " | | Br⁻ | 200 | 25 |
| " | " | " | " | " | o-ClC₆H₄CH₂ | | Cl⁻ | 150 | 48 |
| " | " | " | " | " | propargyl | | Br⁻ | 50 | 22 |
| " | " | " | " | " | m-ClC₆H₄CH₂— | | Cl⁻ | 40 | 22 |
| " | " | " | " | " | 2,4-Cl₂C₆H₃CH₂— | | Cl⁻ | 25 | 38 |
| " | " | CH₃ | Ph | " | — | | — | 150 | 47 |

Similarly, the following 1',2'-cyclohexylene derivatives were evaluated relative to their antiinflammatory effects.

TABLE II-B

| Compound | Dose (mg/kg) | Reduction (%) |
|---|---|---|
| cyclohexylene-thiazoline with CH₃, · HBr | 10 | 46 |
| trans isomer, · HCl | 25, 50 | 76, 100 |
| cis isomer, · HCl | 25, 50 | 57, 80 |
| cyclohexylene-thiazoline-CH₂OH, · HCl | 50 | 45 |
| cyclohexyl-substituted, · HBr | 40 | 29 |
| cyclohexylene-thiazoline-CH(CH₃)OH | 150 | 70 |

As is evident from the data in Table II-B, each of the respective cis and trans stereoisomers of compounds containing a 1',2'-cyclohexylene moiety display excellent antiinflammatory activity. Likewise, those compounds comprised of random mixtures of each of the cis and trans stereoisomers are also active antiinflammatory agents. While the pure trans isomers appear to possess slightly greater antiinflammatory activity than the pure cis compounds or the random stereoisomeric mixtures based upon comparative dose-response relationships, preferential selection of a particular compound or stereoisomer will depend, of course, upon the mode of administration and dosage regimen contemplated, the severity of the inflammatory condition to be treated, dosage related adverse effects, if any, observed and analogous considerations.

EXAMPLE 13

Certain of the compounds of the invention were further tested to determine their $ED_{50}$ values. The $ED_{50}$ value is defined as that dose which reduced edema formation by about 25% or more compared with the mean control response (parallel run) in 50% of the animals. Typical results of these tests appear in Table III.

TABLE III

| ED₅₀ vs. CARRAGEENIN ASSAY | | | |
|---|---|---|---|
| Compound | Dose (mg/kg) | ED₅₀ (mg/kg) | Confidence Limits-95% |
| 1 | 25, 75, 100, 150 | 25 | 18–32 |

TABLE III-continued

ED₅₀ vs. CARRAGEENIN ASSAY

| Compound | Dose (mg/kg) | ED₅₀ (mg/kg) | Confidence Limits-95% |
|---|---|---|---|
| 9 | 25, 50, 75, 100 | 20 | 16–24 |

EXAMPLE 14

Next, certain of the compounds were subjected to a secondary screen designated the adrenalectomized assay. In this series of tests, the method used was identical to that described above, except that the animals used were adrenalectomized several days prior to assay. Since the results in the nonadrenalectomized animals were similar to those obtained in the adrenalectomized animals, it can be inferred that the antiinflammatory activity of the test compounds was not caused by the release of endogeneous adrenocortical steriods.

The results of this test are given in Table IV.

TABLE IV

Adrenalectomized Sprague Dawley Male Rats (Charles River)

| Compound | % Reduction | Dose at mg/kg |
|---|---|---|
| 1 | 32 | 50 |
| 4 | 31 | 25 |
| 5 | 15 | 25 |
| 6 | 19 | 25 |
| 8 | 23 | 25 |
| 9 | 46 | 25 |
| 10 | 18 | 50 |
| 16 | 16 | 50 |
| 17 | 60 | 50 |
| 29 | 18 | 25 |

EXAMPLE 15

Selected compounds were further subjected to advanced evaluations. Specifically, in view of the interesting activity of compounds 1 and 9, those compounds were further subjected to the adjuvant-induced arthritis test. This test requires one month (from day 0 to day 31). In the first 17 days (0–17), the disease is in a developing stage, while for the remainder of the month (18–31) the disease is fully developed. The results of this test, given in terms of percent reduction of swelling in the hind paw of the rat are shown in Table V.

The method is essentially that of Newbould, Brit. J. Pharmacol. 21: 127, 1963. The test compounds were studied in the developing arthritis state and in the established arthritic state. Separate groups of twelve rats were administered the compounds orally using methylcellulose as the vehicle. In the study on the developing disease, administration of the test compounds begins on day 1 and on day 2 each animal is injected with 0.05 ml/kg of a 0.5% suspension of heat-killed Mycobacterium tuberculosis into the plantar surface of the left hind paw. Foot volumes were measured by a water displacement device on the day of administration of the Mycobacterium and again on days 3, 10 and 17. The test compounds were administered once daily. Body weights were recorded daily and the animals were examined for the spread of the inflammation and the degree of secondary lesions. For study in the established disease, another group of rats are injected with the Mycobacterium and foot volumes are measured. After twenty days volumes are again measured and administration of the test compounds begins and continues for eleven days. Foot volume measurements are repeated on day 27 and day 31. The extent of the spread of the inflammation and the degree of lesions are recorded daily as are the body weights. The effect of the test compounds is measured by the percentage reduction in left hind paw volumes as compared to the hind paw volumes of the control groups.

TABLE V

ADJUVANT ARTHRITIS TEST IN RATS
% REDUCTION IN SWELLING-HIND PAWS

| | | Days | | | | |
|---|---|---|---|---|---|---|
| | | Developing (prophylatic) | | Developed (therapeutic) | | |
| Compound | Dose (mg/kg) | 3 | 10 | 17 | 20 | 27 | 31 |
| 1 | 20 | 18 | 13 | 18 | 5 | 0 | 0 |
| | 40 | 10 | 21 | 43 | 4 | 14 | 8 |
| 9 | 24 | 21 | 23 | 15 | 5 | 0 | 0 |
| | 50 | 18 | 17 | 6 | 3 | 3 | 7 |

In addition to the reduction in inflammation indicated in Table V, a lessening in the degree of secondary lesions are observed.

What is claimed is:

1. A compound of the formula

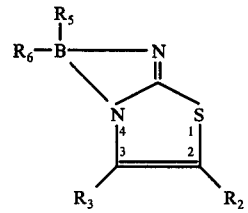

wherein B is 1',2'-cyclohexylene, $R_2$ is hydrogen and $R_3$ is $C_1$–$C_4$ alkyl or phenyl and $R_5$ and $R_6$ are each hydrogen or when $R_3$ is methyl the bond of unsaturation at the 2,3-position of the thiazole ring is saturated and the C-3 carbon atom thereof optionally substituted by a hydroxyl group and $R_5$ and $R_6$ are each hydrogen or the pharmaceutically acceptable inorganic or organic acid addition or quaternary salt thereof.

2. The compound as defined in claim 1 wherein B is 1',2'-cyclohexylene and said compound is selected from the group consisting of cis-3-methyl-4,5,6,7,8,9-hexahydrobenzimidazole thiazole, trans-3-methyl-4,5,6,7,8,9-hexahydrobenzimidazole thiazole, trans-3-methyl-3-hydroxy-2,3,4,5,6,7,8,9-octahydrobenzimidazole thiazole, pharmaceutically acceptable salts and stereoisomeric mixtures thereof.

3. A pharmaceutical antiinflammatory preparation in dosage unit form comprised of a pharmaceutical carrier and a nontoxic antiinflammatory amount of a compound of the formula

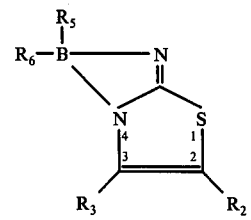

wherein B is 1',2'-cyclohexylene, $R_2$ is hydrogen and $R_3$ is $C_1$–$C_4$ alkyl or phenyl and $R_5$ and $R_6$ are each hydrogen or when $R_3$ is methyl the bond of unsaturation at the 2,3-position of the thiazole ring is saturated and the C-3 carbon atom thereof optionally substituted by a hydroxyl group and $R_5$ and $R_6$ are each hydrogen or the pharmaceutically acceptable inorganic or organic acid addition or quaternary salt thereof.

4. The pharmaceutical antiinflammatory preparation as defined in claim 3 wherein said dosage unit form is adapted for oral administration.

5. The pharmaceutical antiinflammatory preparation as defined in claim 3 wherein said dosage unit form is adapted for parenteral administration.

6. The pharmaceutical antiinflammatory preparation as defined in claim 3 wherein said nontoxic antiinflammatory amount ranges between about 10 to 500 mg/kg/day.

7. A method of preventing and inhibiting the formation of granuloma tissue in an animal subject, which method comprises administering to said animal a nontoxic antiinflammatory amount of a compound of the formula

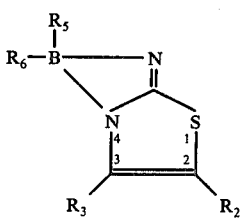

wherein B is 1',2'-cyclohexylene, $R_2$ is hydrogen and $R_3$ is $C_1$–$C_4$ alkyl or phenyl and $R_5$ and $R_6$ are each hydrogen or when $R_3$ is methyl the bond of unsaturation at the 2,3-position of the thiazole ring is saturated and the C-3 carbon atom thereof optionally substituted by a hydroxyl group and $R_5$ and $R_6$ are each hydrogen or the pharmaceutically acceptable inorganic or organic acid addition or quaternary salt thereof.

8. The method as defined in claim 7 wherein the amount administered ranges between about 10 to 500 mg/kg/day.

9. The method as defined in claim 7 wherein said compound is cis-3-methyl-4,5,6,7,8,9-hexahydrobenzimidazole thiazole.

10. A method of preventing and inhibiting the formation of granuloma tissue in an animal subject, which method comprises administering to said animal the pharmaceutical antiinflammatory preparation as defined in claim 3.

* * * * *